US00PP27758P3

(12) United States Plant Patent
Verwer

(10) Patent No.: US PP27,758 P3
(45) Date of Patent: Mar. 7, 2017

(54) ***DAHLIA* PLANT NAMED 'KARMA AMORA'**

(50) Latin Name: *Dahlia hybrida*
Varietal Denomination: Karma Amora

(71) Applicant: Aad W. M. Verwer, Lisse (NL)

(72) Inventor: Aad W. M. Verwer, Lisse (NL)

(73) Assignee: Verwer Dahlias B.V., Lisse (NL)

( * ) Notice: Subject to any disclaimer, the term of this patent is extended or adjusted under 35 U.S.C. 154(b) by 62 days.

(21) Appl. No.: 14/545,628

(22) Filed: May 29, 2015

(65) Prior Publication Data

US 2016/0353642 P1 Dec. 1, 2016

(51) Int. Cl.
*A01H 5/02* (2006.01)

(52) U.S. Cl.
USPC ..... Plt./321

(58) Field of Classification Search
USPC ..... Plt./321
See application file for complete search history.

*Primary Examiner* — June Hwu
(74) *Attorney, Agent, or Firm* — C. A. Whealy

(57) ABSTRACT

A new and distinct cultivar of *Dahlia* plant named 'Karma Amora', characterized by its upright plant habit; high production of flowering stems; dark green-colored leaves; freely flowering habit; decorative-type inflorescence form; large inflorescences with red-colored ray florets that resist fading; and good postproduction longevity.

2 Drawing Sheets

Botanical designation: *Dahlia hybrida.*
Cultivar denomination: 'KARMA AMORA'.

BACKGROUND OF THE INVENTION

The present invention relates to a new and distinct cultivar of *Dahlia* plant, botanically known as *Dahlia hybrida*, and hereinafter referred to by the name 'Karma Amora'.

The new *Dahlia* plant is a product of a planned breeding program conducted by the Inventor in Lisse, The Netherlands. The objective of the breeding program is to create new cut flower *Dahlia* plants with strong flowering stems, large inflorescences and good postproduction longevity.

The new *Dahlia* plant originated from a cross-pollination during the summer of 2005 of *Dahlia hybrida* 'Garden Miracle', not patented, as the female, or seed, parent with *Dahlia hybrida* 'GH Lammerse', not patented, as the male, or pollen, parent. The new *Dahlia* plant was discovered and selected by the Inventor as a single flowering plant from within the progeny of the stated cross-pollination in a controlled greenhouse environment in Lisse, The Netherlands in 2007.

Asexual reproduction of the new *Dahlia* plant by cuttings since the spring of 2008 in a controlled greenhouse environment in Lisse, The Netherlands, has shown that the unique features of this new *Dahlia* plant are stable and reproduced true to type in successive generations.

SUMMARY OF THE INVENTION

Plants of the new *Dahlia* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'Karma Amora'. These characteristics in combination distinguish 'Karma Amora' as a new and distinct *Dahlia* plant:

1. Upright plant habit.
2. High production of flowering stems.
3. Dark green-colored leaves.
4. Freely flowering habit.
5. Decorative-type inflorescence form.
6. Large inflorescences with red-colored ray florets that resist fading.
7. Good postproduction longevity.

Plants of the new *Dahlia* differ primarily from plants of the female parent, 'Garden Miracle', in the following characteristics:

1. Plants of the new *Dahlia* are taller than plants of 'Garden Miracle'.
2. Plants of the new *Dahlia* are more freely branching and produce more flowering stems than plants of 'Garden Miracle'.
3. Plant of the new *Dahlia* and 'Garden Miracle' differ in leaf color as plants of 'Garden Miracle' have bronze-colored leaves.
4. Inflorescences of plants of the new *Dahlia* are longer-lasting than inflorescences of plants of 'Garden Miracle'.

Plants of the new *Dahlia* differ primarily from plants of the male parent, 'GH Lammerse', in the following characteristics:

1. Plants of the new *Dahlia* and 'GH Lammerse' differ in ray floret color as plants of 'GH Lammerse' have purple-colored ray florets.
2. Inflorescences of plants of the new *Dahlia* are longer-lasting than inflorescences of plants of 'GH Lammerse'.

Plants of the new *Dahlia* can be compared to plants of the *Dahlia hybrida* 'Karma Royal Sea', disclosed in U.S. Plant Pat. No. 18,440. In side-by-side comparisons conducted in Lisse, The Netherlands, plants of the new *Dahlia* differed from plants of 'Karma Royal Sea' in the following characteristics:

1. Plants of the new *Dahlia* were more freely branching and produced more flowering stems than plants of 'Karma Royal Sea'.
2. Plants of the new *Dahlia* flowered earlier than plants of 'Karma Royal Sea'.
3. Plants of the new *Dahlia* and 'Karma Royal Sea' differed in ray color as plants of 'Karma Royal Sea' had deep red-colored ray florets.

Plants of the new *Dahlia* can be compared to plants of the *Dahlia hybrida* 'Karma Thalia', disclosed in U.S. Plant Pat. No. 11,406. In side-by-side comparisons conducted in Lisse, The Netherlands, plants of the new *Dahlia* differed from plants of 'Karma Thalia' in the following characteristics:

1. Plants of the new *Dahlia* were more freely branching and produced more flowering stems than plants of 'Karma Thalia'.
2. Plants of the new *Dahlia* and 'Karma Thalia' differed in ray color as plants of 'Karma Thalia' had red purple-colored ray florets.

BRIEF DESCRIPTION OF THE PHOTOGRAPHS

The accompanying photographs illustrate the overall appearance of the new *Dahlia* plant showing the colors as true as it is reasonably possible to obtain in colored reproductions of this type. Colors in the photographs may differ slightly from the color values cited in the detailed botanical description which accurately describe the colors of the new *Dahlia* plant.

The photograph on the first sheet comprises a side perspective view of typical flowering stems of 'Karma Amora' grown in an outdoor nursery.

The photograph on the second sheet is a close-up view of a typical inflorescence of 'Karma Amora'.

DETAILED BOTANICAL DESCRIPTION

The photographs and following observations and measurements describe plants grown during the late summer and early autumn in ground beds in an outdoor nursery in Lisse, The Netherlands and under cultural practices typical of commercial *Dahlia* production. During the production of the plants, day temperatures ranged from 12° C. to 29° C. and night temperatures ranged from 6° C. to 19° C. Plants were pinched one time about three weeks after planting. Plants were three months old when the photographs and the description were taken. In the following description, color references are made to The Royal Horticultural Society Colour Chart, 1995 Edition, except where general terms of ordinary dictionary significance are used.

Botanical classification: *Dahlia hybrida* 'Karma Amora'.

Parentage:

*Female, or seed, parent.*—*Dahlia hybrida* 'Garden Miracle', not patented.

*Male, or pollen, parent.*—*Dahlia hybrida* 'GH Lammerse', not patented.

Propagation:

*Type.*—By vegetative cuttings.

*Time to initiate roots, summer.*—About ten to twelve days at soil temperatures about 15° C. and air temperatures about 20° C. to 22° C.

*Time to initiate roots, winter.*—About 12 to 14 days at soil temperatures about 15° C. and air temperatures about 20° C. to 22° C.

*Time to produce a rooted young plant, summer.*—About 21 days at soil temperatures about 15° C. and air temperatures about 20° C. to 22° C.

*Time to produce a rooted young plant, winter.*—About 25 days at soil temperatures about 15° C. and air temperatures about 20° C. to 22° C.

*Root description.*—Fine, fleshy; white in color.

*Rooting habit.*—Freely branching; dense.

*Tubers.*—Length: About 20 cm. Diameter: About 22 cm. Texture: Corky. Color: Close to 199B, actual color depends on actual soil composition.

Plant description:

*Plant and growth habit.*—Upright plant habit; narrow inverted triangular plant form; freely basal branching with about eight primary lateral branches developing per plant; dense and bushy appearance; good production of flowering stems; inflorescences held above the foliar plane on strong peduncles; vigorous growth habit.

*Plant height.*—About 100 cm.

*Plant diameter or spread.*—About 50 cm.

*Lateral branches.*—Length: About 30 cm to 40 cm. Diameter: About 3 cm. Internode length: About 5 cm to 14 cm. Texture: Smooth, glabrous. Strength: Strong. Aspect: Erect to about 10° from vertical. Color: Close to 144A tinged with close to 187A.

Leaf description:

*Arrangement.*—Opposite, simple or compound with three or five leaflets per leaf.

*Leaf length, simple leaves.*—About 9 cm.

*Leaf width, simple leaves.*—About 3.5 cm.

*Leaf length, compound leaves with three leaflets.*—About 15 cm.

*Leaf width, compound leaves with three leaflets.*—About 13 cm.

*Leaf length, compound leaves with five leaflets.*—About 25 cm.

*Leaf width, compound leaves with five leaflets.*—About 18 cm.

*Shape, simple leaves or leaflets.*—Ovate.

*Apex, simple leaves or leaflets.*—Acuminate.

*Base, simple leaves or leaflets.*—Attenuate.

*Margin, simple leaves or leaflets.*—Serrate; sinuses divergent.

*Venation pattern, simple leaves or leaflets.*—Pinnate, reticulate.

*Texture, upper and lower surfaces, simple leaves or leaflets.*—Smooth, glabrous.

*Color.*—Developing and fully expanded leaves or leaflets, upper surface: Close to 137A. Developing and fully expanded leaves or leaflets, lower surface: Darker than 191A.

*Petioles.*—Length, simple leaves: About 1 cm. Length, compound leaves with three leaflets: About 2.5 cm. Length, compound leaves with five leaflets: About 5 cm. Diameter, simple leaves or leaflets: About 4 mm. Texture, upper and lower surfaces, simple leaves or leaflets: Smooth, glabrous. Color, simple leaves or leaflets: Upper surface: Close to 153A tinted with close to 183B. Lower surface: Close to 148B.

Inflorescence description:

*Appearance and flowering habit.*—Hemispherical decorative-type inflorescences with ray and disc florets developing acropetally on a receptacle; inflorescences positioned above and beyond the foliar plane on strong peduncles; inflorescences face mostly upright; freely flowering habit with typically about 88 inflorescences developing per plant.

*Fragrance*.—None detected.

*Time to flower*.—Early flowering habit; plants begin flowering about 80 days after planting; flowering continuous during the summer and autumn in The Netherlands.

*Post-production longevity*.—Good postproduction longevity; inflorescences maintain good substance for about 16 days on the plant and for about seven days as a cut flower; inflorescences persistent.

*Inflorescence buds*.—Height: About 1.7 cm. Diameter: About 2.3 cm. Shape: Oblate. Texture: Smooth, glabrous. Color: Towards the base, close to 144A; mid-section, close to 144A and 183A; towards the apex, close to 153A.

*Inflorescence diameter*.—About 13 cm.

*Inflorescence depth* (*height*).—About 6.8 cm.

*Disc diameter*.—About 7 mm.

*Receptacle height*.—About 1.8 cm.

*Receptacle diameter*.—About 1.6 cm.

*Receptacle color*.—Close to 153A.

*Ray florets*.—Number of ray florets per inflorescence: About 130 arranged in about 16 whorls. Length: About 6.8 cm. Width: About 2.8 cm. Shape: Ovate. Apex: Obtuse. Base: Attenuate. Margin: Entire. Aspect: Initially upright to roughly perpendicular to the peduncle, reflexing with development. Texture, upper and lower surfaces: Smooth, glabrous; velvety. Color: When opening, upper surface: Close to 187B. When opening, lower surface: Close to 187C; towards the base and along the veins, close to 4C. Fully opened, upper surface: Close to 45A; color does not fade with development. Fully opened, lower surface: Close to 45B; along the veins, close to 72B; color does not fade with development.

*Disc florets*.—Number of disc florets per inflorescence: About twelve, inconspicuous. Length: About 9 mm. Diameter: About 0.3 mm. Shape: Tubular; apex dentate. Aspect: Mostly upright. Texture: Smooth, glabrous. Color, immature: Apex: Close to 166A. Mid-section: Close to 17A. Base: Close to 1C. Color, mature: Apex: Close to 17B. Mid-section: Close to 17A. Base: Close to 1C.

*Phyllaries*.—Quantity per inflorescence: About eight arranged in a single whorl. Length: About 1.6 cm. Width: About 1 cm. Shape: Ovate. Apex: Acute. Base: Attenuate. Margin: Entire. Texture, upper and lower surfaces: Smooth, glabrous. Color, upper surface: Close to 146A tinted with close to 187B. Color, lower surface: Close to 146B.

*Peduncles*.—Length, terminal peduncle: About 14 cm to 20 cm. Length, fourth peduncle: About 12 cm. Length, seventh peduncle: About 10 cm. Diameter: About 5 mm. Strength: Strong. Aspect: Mostly erect. Texture: Smooth, glabrous. Color: Close to 144A tinted with close to 183A.

*Reproductive organs*.—Androecium, present on disc florets only: Quantity per disc floret: Five. Filament length: About 1.3 cm. Filament color: Close to 1D. Anther length: About 3 mm. Anther shape: Lanceolate. Anther color: Close to 23B. Pollen amount: Moderate. Pollen color: Close to 21B. Gynoecium, present on ray and disc florets: Quantity per floret: One. Pistil length: About 5 mm. Stigma shape: Lanceolate. Stigma color: Close to 2B. Style length: About 3 mm. Style color: Close to 1C. Ovary color: Close to 178C. Fruits: Length: About 2 cm. Diameter: About 2 cm. Texture: Smooth, glabrous. Color: Close to 200A. Seeds: Quantity per fruit: About 25. Length: About 8 mm. Diameter: About 1.5 mm. Color: Close to 200A.

Disease & pest resistance: Plants of the new *Dahlia* have not been shown to be resistant to pathogens and pests common to *Dahlia* plants.

Garden performance: Plants of the new *Dahlia* have exhibited good tolerance to rain and wind and have been observed to tolerate temperatures from about 0° C. to about 35° C.

It is claimed:

1. A new and distinct *Dahlia* plant named 'Karma Amora' as illustrated and described.

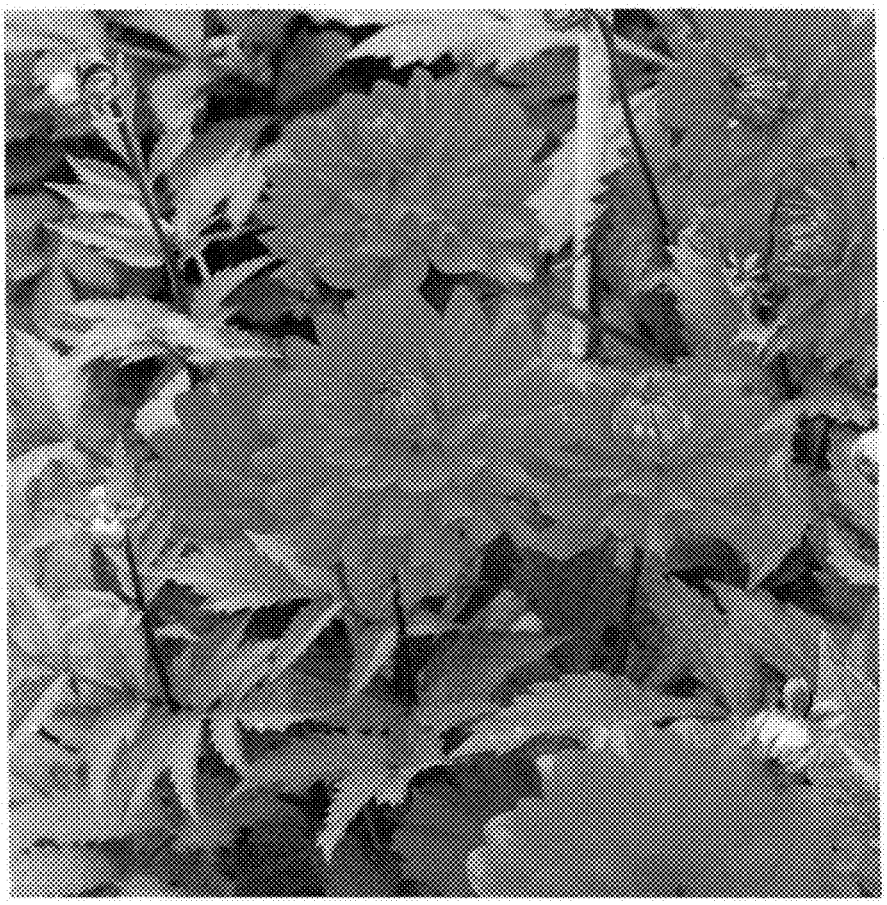

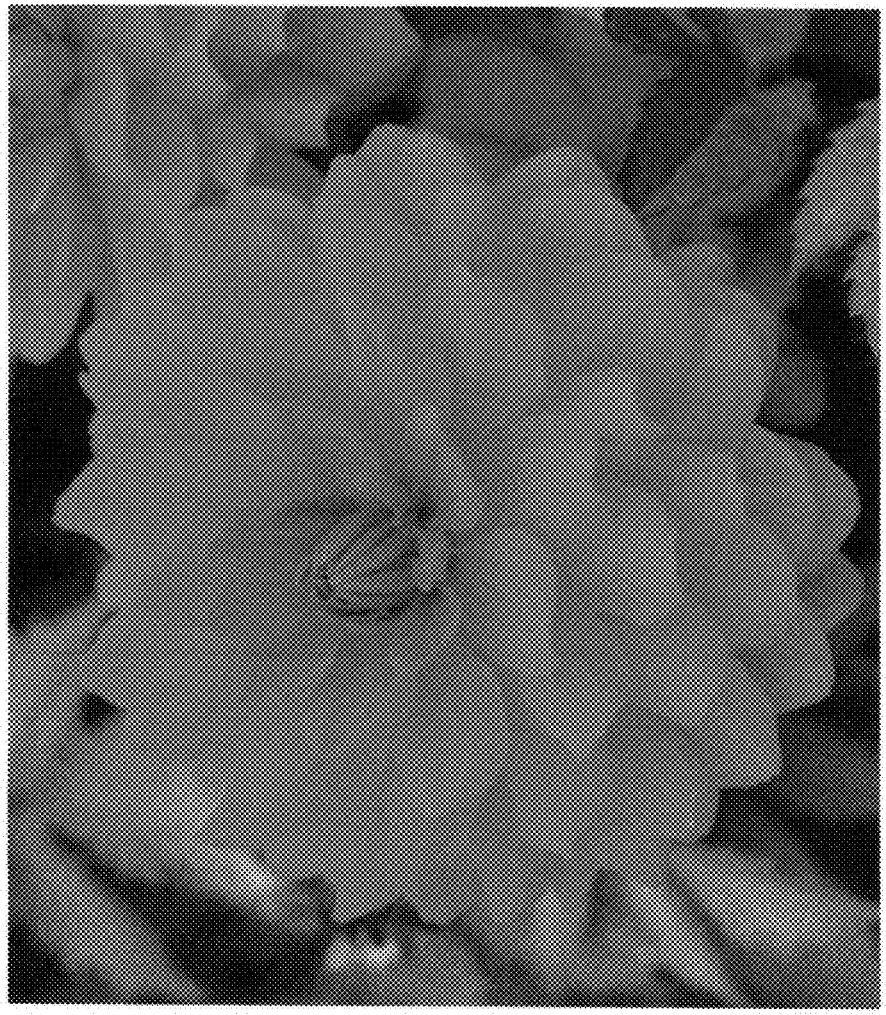

* * * * *